United States Patent
Bombardelli et al.

(10) Patent No.: US 9,770,475 B2
(45) Date of Patent: Sep. 26, 2017

(54) COMPOSITIONS FOR THE TREATMENT OF PERIPHERAL ULCERS OF VARIOUS ORIGINS

(75) Inventors: Ezio Bombardelli, Gropello Cairoli (IT); Paolo Morazzoni, Milan (IT); Massimo Ronchi, Milan (IT)

(73) Assignee: INDENA S.P.A., Milan (IT)

( * ) Notice: Subject to any disclaimer, the term of this patent is extended or adjusted under 35 U.S.C. 154(b) by 932 days.

(21) Appl. No.: 13/881,412

(22) PCT Filed: Oct. 21, 2011

(86) PCT No.: PCT/EP2011/068399
§ 371 (c)(1),
(2), (4) Date: Apr. 25, 2013

(87) PCT Pub. No.: WO2012/055774
PCT Pub. Date: May 3, 2012

(65) Prior Publication Data
US 2013/0236575 A1    Sep. 12, 2013

(30) Foreign Application Priority Data
Oct. 28, 2010 (IT) .............................. MI2010A2009

(51) Int. Cl.
| | | |
|---|---|---|
| A61K 36/28 | (2006.01) | |
| A61K 31/70 | (2006.01) | |
| A61K 36/45 | (2006.01) | |
| A61K 36/77 | (2006.01) | |
| A61K 36/87 | (2006.01) | |
| A61K 45/06 | (2006.01) | |
| A61K 31/352 | (2006.01) | |
| A61K 31/353 | (2006.01) | |

(52) U.S. Cl.
CPC ............ *A61K 36/28* (2013.01); *A61K 31/352* (2013.01); *A61K 31/353* (2013.01); *A61K 31/70* (2013.01); *A61K 36/45* (2013.01); *A61K 36/77* (2013.01); *A61K 36/87* (2013.01); *A61K 45/06* (2013.01)

(58) Field of Classification Search
CPC ...................................................... A61K 36/00
USPC ......................................................... 424/725
See application file for complete search history.

(56) References Cited

U.S. PATENT DOCUMENTS

| | | | |
|---|---|---|---|
| 2008/0026058 A1* | 1/2008 | Bombardelli | A61K 31/352 424/468 |
| 2008/0145319 A1 | 6/2008 | Bombardelli et al. | |
| 2009/0155377 A1* | 6/2009 | Olalde Rangel | A61K 36/28 424/548 |
| 2010/0310684 A1 | 12/2010 | Bombardelli et al. | |
| 2011/0206792 A1 | 8/2011 | Tutino | |

OTHER PUBLICATIONS

Bohl, R., et al., Interim Communication on the Favourable Results Obtained by Treating Pressure . . . , Schweizerische Medizinische Wochenschrift 1954, vol. 84, No. 15, 1954, Xp009149411.
Mian, et al., Anthocyanosides and Microvessel Wall: New Insights on the Mode . . . , Minerva Medica Oct. 31, 1977, vol. 68, No. 52, XP009149405.
Yarnell, et al., Botanical Medicines for Dermatologic Conditions, Alternative and Complementary Therapies, vol. 5, No. 2, pp. 106-109, 1999.
Pullen, et al., Multicentre Evaluation of the Topical . . . , European Journal of Geriatrics, vol. 2, No. 1, pp. 27-30, 2000.
Madhan, et al., Stabilization of Collagen Using Plant Polyphenol . . . , International Journal of Biological Macromolecules, vol. 37, No. 1-2, pp. 47-53, 2005.
Portugal, et al., Interplay Among Oxidants, Antioxidants, and Cytokines in Skin . . . , Biomedicine and Pharmacotherapy, vol. 61, No. 7, pp. 412-422, 2007.
Draelos Z.. D., Topical Anti-Inflammatory Agents, vol. 16, No. 10, pp. 41-42, 2003.
International Preliminary Report issued in counterpart International PCT Application No. PCT/EP2011/068399.
International Search Report issued in counterpart International PCT Application No. PCT/EP2011/068399.

* cited by examiner

*Primary Examiner* — Michael Meller
(74) *Attorney, Agent, or Firm* — Silvia Salvadori, P.C.; Silvia Salvadori

(57) ABSTRACT

The present invention relates to compositions containing a combination of a cell proliferation-stimulating agent with vasokinetic properties and an antimicrobial, antifungal and antiviral agent with an anti-inflammatory/analgesic, which is useful in the treatment of peripheral ulcers of various origins, such as diabetic ulcers, ulcers caused by venous stasis of the limbs, bedsores and the associated skin infections. Said combination could be presented as formulations for topical or systemic use.

6 Claims, No Drawings

COMPOSITIONS FOR THE TREATMENT OF PERIPHERAL ULCERS OF VARIOUS ORIGINS

SUMMARY OF THE INVENTION

The present invention relates to compositions containing a combination of a cell proliferation-stimulating agent with vasokinetic properties and an antimicrobial, antifungal and antiviral agent with an anti-inflammatory/analgesic, which is useful in the treatment of peripheral ulcers of various origins, such as diabetic ulcers, ulcers caused by venous stasis of the limbs, bedsores and the associated skin infections. More particularly, the present invention relates to compositions containing catechin polyphenols, anthocyanosides, or *Aesculus hippocastanum, Vitis vinifera* or Ericaceae extracts containing them, and *Echinacea* sp. extract.

Said compositions are suitable for topical or systemic use.

TECHNICAL BACKGROUND

Disorders like peripheral ulcers, whether they are diabetic ulcers, ulcers caused by venous stasis of the limbs, or bedsores and the associated skin infections, have different etiologies although they present common symptoms. Some involve the peripheral circulation and microcirculation, while many are associated with arteriosclerosis which causes occlusions of the small and medium arteries with consequent oedema and, due to accidental causes or scratching caused by itching, can result in a lesion that is difficult to heal due to subsequent bacterial and/or fungal infection.

Ulcers associated with chronic venous insufficiency require lengthy treatments with a combination of substances having different, synergic actions. Diabetic ulcers have similar origins to the former, and are accompanied by peripheral pain and purpura.

Vasokinetic and vasoprotective agents generally improve wound healing, especially in the case of bedsores. The availability of substances which have a wound-healing and vasokinetic action, together with substances which rapidly eliminate infection and pain, would therefore be desirable. Keeping the arterial microcirculation active and removing protein seepage from the ulcerated area by means of lymph drainage further accelerates tissue re-epithelialisation.

DESCRIPTION OF THE INVENTION

It has been found that the combination of catechin polyphenols or anthocyanosides and *Echinacea* sp. extract induces surprisingly rapid wound healing, with a reduction of the surrounding oedema and re-epithelialisation, due to the immediate reduction of fibrin production and protein seepage, which allows wound cleaning and rapid proliferation of granulation tissue.

The present invention therefore relates to compositions containing, as active ingredients:

a) catechin polyphenols or anthocyanosides or extracts containing them, and b) *Echinacea* sp. Extract for the treatment of peripheral ulcers of various origins, such as stasis ulcers, diabetic ulcers, bedsores and the associated skin infections.

Catechin polyphenols are known to possess in vitro activity on fibroblast proliferation, antiprotease activity on the ground substance of connective tissue, and vasokinetic activity at venous and lymphatic level. According to the present invention, said polyphenols can be present either as single molecules or in the form of extracts containing them. When they are present in the form of extracts, *Aesculus hippocastanum* or *Vitis vinifera* extracts will preferably be used. Said extracts will preferably be obtained by extraction from the aerial parts of said plants.

According to a preferred aspect, the catechin polyphenols will be present in the form of an extract obtained from *Aesculus hippocastanum* bark, branches and fruit pericarp. Said extract basically contains two classes of substance: procyanidin A2, which is not only a powerful protease inhibitor but also active as a microvasculokinetic agent at venous and lymphatic level, and significant amounts of esculoside, a powerful vasokinetic agent at arterial level.

According to a preferred aspect, the catechin polyphenols will be selected from alcoholic extract of *Aesculus hippocastanum*, proanthocyanidin A2, and oligomeric proanthocyanidins extracted from *Vitis vinifera* seeds.

According to a preferred aspect, the term "anthocyanosides" comprises both anthocyanosides properly so called and their aglycons (anthocyanidins).

The anthocyanosides are preferably derived from Ericacea extracts, in particular extracts of various species of *Vaccinium*.

According to a preferred aspect the anthocyanosides are derived from cranberry fruit and leaf extracts (*Vaccinium macrocarpon, V. oxycoccus, V. erythrocarpum, V. microcarpum, V. oxycoccos*).

According to a further preferred aspect the anthocyanosides are derived from a *Vaccinium myrtillus* extract. Bilberry (*Vaccinium myrtillus*) extract is a product with marked anti-inflammatory activity, especially at topical level, due to its effect on capillary fragility and permeability. The preparation of bilberry extracts containing anthocyanosides is known. Moreover, bilberry anthocyanosides, like procyanidins, have a bacteriostatic action which prevents bacterial and fungal adherence.

*Echinacea* extract exerts an analgesic, antiviral, anti-inflammatory and antimicrobial activity, leading to a global improvement in wound healing; it also has a significant effect on all forms of itching, a condition that often accompanies the formation of sores caused by venostasis, and is useful in the healing, and above all prevention, of sores.

According to a preferred aspect of the invention, the *Echinacea* sp extract is an alcoholic extract of *Echinacea angustifolia* or *purpurea*.

The percentages of active ingredients can range between 0.05 and 2% for catechin polyphenols, anthocyanosides, or extracts containing them, whereas for *Echinacea* sp. extract, the concentrations can range between 0.01 and 1%.

According to a preferred aspect, the compositions according to the invention will therefore contain the active ingredients within the following percentage intervals:

a) catechin polyphenols, anthocyanosides, or extracts containing them: 0.05 to 2%;

b) *Echinacea* sp. extract: 0.01 to 1%.

According to a particularly preferred aspect, the compositions will contain the active ingredients within the following percentage intervals:

a) catechin polyphenols, anthocyanosides, or extracts containing them: 0.1 to 1%;

b) *Echinacea* sp extract: 0.05 to 0.5%.

The compositions according to the invention can be administered topically or systemically, for example as water/oil emulsions, aseptic dusting powders or occlusive formulations.

According to a preferred aspect, the occlusive formulations will be in solid form, designed to be hydrated at the time of application, containing alginic acid as gelling polysaccharide.

The preferred excipients for use in the formulations are polysaccharides, such as hyaluronic acid and chondroitin sulphate or alginic acid, which help to form a protective film that stimulates wound healing.

In human pharmacological treatment the formulations are applied to the wound, and left to be absorbed. Particularly infected wounds should be covered with sticking plaster to form an occlusive dressing. The wound treatment is repeated one to three times a day, taking care to protect the wound or sore against mechanical traumas.

The compositions according to the invention will be prepared according to well-known conventional methods, such as those described in "Remington's Pharmaceutical Handbook", Mack Publishing Co., N.Y., USA, together with suitable excipients.

The following examples illustrate the invention in detail.

PREPARATION EXAMPLES

Example 1—Preparation of *Aesculus hippocastanum* Bark Extract

Procyanidin A2 and esculoside are repeatedly extracted from 5 Kg of bark from finely ground *Aesculus hippocastanum* branches with 95% ethanol until exhausted. The extraction solvent is concentrated to an equal weight with the starting biomass, and the concentrate is filtered to eliminate undesirable substances. The filtrate is concentrated until dry under vacuum at a temperature not exceeding 40° C. 570 g of a beige extract with a 35% esculoside content and an 11.2% procyanidin A2 is obtained. This extract can be used "as is" in the formulations according to the invention.

Example 2—Preparation of *Echinacea angustifolia* Root Extract

Echinacoside, caffeoylquinic acids and isobutylamides are extracted from 2 Kg of finely ground *Echinacea angustifolia* roots with 95% ethanol at the temperature of 50° C. until exhausted. Thin-layer chromatography is used to test for exhaustion, with echinacoside as the marker. The extraction solvent is concentrated under vacuum at a temperature of 25° C., taking care not to distil the basic oil containing the isobutylamides in steam current. By concentrating the solvent until dry, 150 g of extract with a 4% echinacoside content and an 0.5% isobutylamide content is obtained. This extract can be used "as is" in the formulations according to the invention.

PHARMACOLOGICAL EXAMPLE

Example 3—Effect on Ulcers Caused by Venous Stasis of the Lower Limbs 50 patients (10 per group), suffering from venous stasis ulcers of the lower limbs, not complicated by other vascular disorders, were included in the study.

The patients were treated with the preparation described in example 8, applied to the lesion twice a day. The treated lesions were then covered with a bandage to ensure that the cream was not removed, and to protect them against external agents and/or mechanical traumas. The lesions were monitored for 21 days, and re-epithelialisation was assessed by measuring the two diameters. The results were expressed as the mean of the two diameters measured.

The results are set out in the table below.

| TREATMENT | RE-EPITHELIALISATION | | |
|---|---|---|---|
| | 7 days | 14 days | 28 days |
| Placebo | 0.02 V 0.01 | 0.01 ± 0.01 | 0.03 ± 0.02 |
| Preparation example 8 | 2.14 ± 0.73** | 4.9 ± 1.01** | 8.30 ± 1.10** |
| Placebo + *Vaccinium myrtillus* 0.3% | 0.10 ± 0.03 | 0.23 ± 0.13* | 0.50 ± 0.23* |
| Placebo + *Echinacea angustifolia* 0.3% | 0.01 ± 0.01 | 0.20 ± 0.02* | 0.35 ± 0.02* |

*$P < 0.05$;
**$P < 0.001$ Student's "t" test

Some formulation examples are set out below.

FORMULATION EXAMPLES

Example 4—Granulate for Sachets Used to Prepare an Extempore Aqueous Gel

| | |
|---|---|
| *Aesculus hippocastanum* (bark extract) | 0.5 g |
| *Echinacea angustifolia* (root extract) | 0.1 g |
| Alginic acid as calcium salt | 0.5 g |
| Carboxymethylcellulose sodium salt | 0.3 g |
| Sorbitol | 1.2 g |

Example 5—Aqueous Gel

| | |
|---|---|
| *Aesculus hippocastanum* (bark extract) | 0.5 g |
| *Echinacea angustifolia* (root extract) | 0.1 g |
| Alginic acid as calcium salt | 0.5 g |
| Propylene glycol | 5.0 g |
| Carboxymethylcellulose sodium salt | 3.5 g |
| Potassium sorbate | 0.1 g |
| Purified water q.s. for | 100.0 g |

Example 6—Dusting Powder

| | |
|---|---|
| *Vitis vinifera* (seed extract) | 1.0% |
| *Echinacea angustifolia* (root extract) | 0.2% |
| Colloidal silicon dioxide | 2.0% |
| Talc q.s. for | 100.0% |

Example 7—Aqueous Gel

| | |
|---|---|
| *Vitis vinifera* | 0.50 g |
| *Echinacea angustifolia* (root extract) | 0.10 g |
| Polyethylene glycol 400 | 5.00 g |
| Glycerin | 5.00 g |
| Carbomer | 1.00 g |
| Sodium hydroxide 10% solution | 2.00 g |
| Methyl paraben | 0.20 g |
| Propylparaben | 0.05 g |
| Potassium sorbate | 0.15 g |
| Purified water q.s. for | 100 g |

Example 8—Cream (O/W Emulsion)

| | | |
|---|---:|---|
| *Vaccinium myrtillus* dried extract | 0.300 | g |
| *Echinacea angustifolia* (root extract) | 0.300 | g |
| Liquid paraffin | 8.000 | g |
| Stearic acid | 10.000 | g |
| Methyl para-hydroxybenzoate | 0.028 | g |
| Propyl para-hydroxybenzoate | 0.012 | g |
| Polysorbate 80 | 2.000 | g |
| Glycerin | 12.000 | g |
| Purified water q.s. for | 100.000 | g |

The invention claimed is:

1. A composition consisting of 0.05% to 2% of an extract of *Vaccinium myrtillus*, 0.01% to 1% of an extract of *Echinacea angustifolia* sp. and pharmaceutically acceptable excipients.

2. The composition of claim 1, wherein the extract of *Echinacea angustifolia* sp. is an alcoholic extract.

3. The composition of claim 1, wherein the extract of *Vaccinium myrtillus* is 0.1 to 1%; and the extract of *Echinacea angustifolia* sp. is 0.05 to 0.5%.

4. The compositions of claim 1, which is in topical or systemic form.

5. A composition consisting of 0.05% to 2% of an extract of *Vaccinium myrtillus,* 0.01% to 1% of an extract of *Echinacea angustifolia* sp. and
pharmaceutically acceptable excipients for the treatment of peripheral ulcers of various origins, and the related skin infections thereof.

6. The composition of claim 5, wherein the ulcers are diabetic ulcers, venous stasis ulcers of the limbs, or bedsores.

* * * * *